US008979755B2

(12) United States Patent
Szydlo-Moore et al.

(10) Patent No.: US 8,979,755 B2
(45) Date of Patent: Mar. 17, 2015

(54) DEVICES AND SYSTEMS FOR REMOTE PHYSIOLOGICAL MONITORING

(75) Inventors: Joanna Szydlo-Moore, Everett, WA (US); Shawn H. Park, Cerritos, CA (US)

(73) Assignee: The Boeing Company, Chicago, IL (US)

( * ) Notice: Subject to any disclaimer, the term of this patent is extended or adjusted under 35 U.S.C. 154(b) by 1820 days.

(21) Appl. No.: 11/608,777

(22) Filed: Dec. 8, 2006

(65) Prior Publication Data

US 2008/0139894 A1     Jun. 12, 2008

(51) Int. Cl.
*A61B 5/00* (2006.01)
*A61B 8/00* (2006.01)
*A61B 5/0408* (2006.01)

(52) U.S. Cl.
CPC ............. *A61B 5/0002* (2013.01); *A61B 5/6833* (2013.01); *A61B 8/4236* (2013.01); *A61B 5/6832* (2013.01); *A61B 5/04085* (2013.01)
USPC ....................................................... 600/301

(58) Field of Classification Search
CPC .......... B82Y 10/00; B82Y 30/00; B82Y 7/24; B82Y 15/00; A61B 5/6833; A61B 2562/046; A61B 2562/066; A61B 2562/164; A61B 5/0245; G06F 19/3418; G06F 19/345; G06F 19/3462; G06F 19/3487; G06F 19/3406; G06F 19/321; G06F 19/322; G06F 19/3456; G06F 17/30386; G06F 19/3412; G06F 19/3437; G06F 19/327; G08B 21/0453; H05K 1/144; H05K 1/0283; H05K 1/147; H05K 1/189; H05K 2201/09263; H05K 3/323

USPC ................................ 600/300–301; 3/300–301
See application file for complete search history.

(56) References Cited

U.S. PATENT DOCUMENTS

| | | | | |
|---|---|---|---|---|
| 5,833,603 A | * | 11/1998 | Kovacs et al. | 600/317 |
| 5,862,803 A | * | 1/1999 | Besson et al. | 600/508 |
| 5,891,185 A | * | 4/1999 | Freed et al. | 607/72 |
| 6,052,624 A | * | 4/2000 | Mann | 607/46 |
| 6,093,146 A | | 7/2000 | Filangeri | |
| 6,230,057 B1 | * | 5/2001 | Chow et al. | 607/54 |
| 6,289,238 B1 | * | 9/2001 | Besson et al. | 600/509 |
| 6,312,393 B1 | * | 11/2001 | Abreu | 600/558 |
| 6,317,630 B1 | * | 11/2001 | Gross et al. | 604/20 |
| 6,385,473 B1 | * | 5/2002 | Haines et al. | 600/393 |
| 6,544,193 B2 | * | 4/2003 | Abreu | 600/558 |
| 6,611,783 B2 | * | 8/2003 | Kelly et al. | 702/150 |

(Continued)

OTHER PUBLICATIONS

J.S. Boland et al., Arrayed Liquid Rotor Electret Power Generator Systems, IEEE 2005, pp. 618-621.

(Continued)

*Primary Examiner* — William Thomson
*Assistant Examiner* — Shirley Jian
(74) *Attorney, Agent, or Firm* — Yee & Associates, P.C.

(57) ABSTRACT

Devices and systems are provided for the remote monitoring of physiological parameters of a patient. An exemplary wireless physiological monitoring device comprises a substrate formed of a flexible biocompatible material. The substrate has a surface for affixing to the skin of a patient. A wireless data transmission device, a biosensor, and a power source are integrated with the substrate. The biosensor is configured to measure a physiological parameter. Flexible conductors are integrated with the substrate and are configured to electrically couple the biosensor and the power source with the data transmission device.

26 Claims, 2 Drawing Sheets

(56) References Cited

U.S. PATENT DOCUMENTS

| | | | |
|---|---|---|---|
| 6,729,336 B2 * | 5/2004 | Da Silva et al. | 128/897 |
| 6,887,202 B2 * | 5/2005 | Currie et al. | 600/309 |
| 6,976,998 B2 * | 12/2005 | Rizzo et al. | 623/6.63 |
| 6,984,207 B1 | 1/2006 | Sullivan et al. | |
| 7,005,179 B2 * | 2/2006 | Davidson et al. | 428/209 |
| 7,120,501 B2 * | 10/2006 | Boylston et al. | 607/57 |
| 7,382,247 B2 * | 6/2008 | Welch et al. | 340/539.12 |
| 7,403,805 B2 * | 7/2008 | Abreu | 600/318 |
| 7,684,868 B2 * | 3/2010 | Tai et al. | 607/54 |
| 8,287,451 B2 * | 10/2012 | Hu et al. | 600/301 |
| 8,688,189 B2 * | 4/2014 | Shennib | 600/382 |
| 2001/0032059 A1 * | 10/2001 | Kelly et al. | 702/150 |
| 2002/0049389 A1 * | 4/2002 | Abreu | 600/558 |
| 2003/0097166 A1 * | 5/2003 | Krulevitch et al. | 607/116 |
| 2003/0139687 A1 * | 7/2003 | Abreu | 600/558 |
| 2003/0158588 A1 * | 8/2003 | Rizzo et al. | 607/54 |
| 2004/0039297 A1 * | 2/2004 | Abreu | 600/558 |
| 2004/0039298 A1 * | 2/2004 | Abreu | 600/558 |
| 2004/0078219 A1 * | 4/2004 | Kaylor et al. | 705/2 |
| 2004/0096959 A1 * | 5/2004 | Stiene et al. | 435/287.2 |
| 2005/0096513 A1 * | 5/2005 | Ozguz et al. | 600/301 |
| 2005/0101841 A9 * | 5/2005 | Kaylor et al. | 600/300 |
| 2006/0049957 A1 * | 3/2006 | Surgenor et al. | 340/825.19 |
| 2006/0058627 A1 * | 3/2006 | Flaherty et al. | 600/409 |
| 2006/0122473 A1 * | 6/2006 | Kill et al. | 600/300 |
| 2007/0123756 A1 * | 5/2007 | Kitajima et al. | 600/300 |
| 2007/0276270 A1 * | 11/2007 | Tran | 600/508 |
| 2008/0259577 A1 * | 10/2008 | Hu et al. | 361/749 |
| 2009/0182204 A1 * | 7/2009 | Semler et al. | 600/301 |

OTHER PUBLICATIONS

W. Li et al., Integrated Flexible Ocular Coil for Power and Data Transfer in Retinal Prostheses, Proceedings of the 2005 IEEE, Sep. 1, 2005, pp. 1028-1031.

Damien C. Rodger et al., Microelectronic Packaging for Retinal Prostheses, IEEE Engineering in Medicine and Biology Magazine, Sep./Oct. 2005, pp. 52-57.

Damien C. Rodger et al., Scalable Flexible Chip-Level Parylene Package for High Lead Count Retinal Prostheses, IEEE 2005, pp. 1973-1976.

"Thin Film Deposition Technologies", IEEE Global History Network, Sep. 2, 2008, pp. 1-3, retrieved Oct. 16, 2009 http://www.ieeeghn.org/wiki/index.php/Thin_Film_Deposition_Technologies.

U.S. Department of Energy—Energy Efficiency and Renewable Energy—Solar Energy Technologies Program, pp. 1-4, retrieved Oct. 13, 2009 http://www1.eere.energy.gov/solar/printabl_versions/tf_polycrystalline.html.

"What is Thin Film", Kyocera Global, pp. 1-4, retrieved Oct. 13, 2009 http://global.kyocera.com/prdct/tfc/tph/tec/thin-film.html.

* cited by examiner

DEVICES AND SYSTEMS FOR REMOTE PHYSIOLOGICAL MONITORING

TECHNICAL FIELD

The embodiments described herein generally relate to physiological monitoring systems, and more particularly relate to portable, non-invasive devices for measuring and monitoring physiological parameters and to systems using such devices for remote monitoring.

BACKGROUND

Physiological monitoring of an animal, such as a human, typically includes the monitoring of vital signs, such as pulse, respiration, and blood pressure. Other physiological data of interest may include blood chemistry information, body temperature, hydration levels, sweat electrolyte information, electrocardiogram data, and the like. This information can be used to assess the health of the intended subject, the physical condition of the subject, or the subject's ability to participate in a given activity.

This physiological data can be relatively easy to measure and monitor in a doctor's or veterinarian's office or hospital. In those instances, the patient can be connected to physiological measurement devices directly coupled to central stations that monitor and record patient data. Such physiological measurement devices typically are dedicated devices that assess a single or related group of physiological parameters. However, various physiological data is often helpful, if not required, when a subject is not in a medical office or hospital and cannot be connected to central monitoring stations, such as when in transit, as from an emergency or accident, or when in a war zone site, where connection to cumbersome monitoring devices is not practical. For example, higher survival rates of soldiers may be possible if various physiological data could be remotely monitored by military medics when the soldiers are on battlefields and when being transported to medical facilities or extended care facilities.

Non-invasive and remote monitoring of various physiological parameters also is helpful to determine if a subject is in condition to perform a selected activity. For example, physiological data could aid in determining if a pilot's physical condition could inhibit her ability to safely fly an aircraft. Similarly, the non-invasive remote monitoring of physiological data of astronauts could indicate remedial measures that the astronauts could take to maintain or improve their health while in space. Non-invasive and remote physiological monitoring systems could also measure various physiological data of automobile drivers or other heavy-machinery operators and transmit that data to devices that would disable the engines of the machinery when high blood alcohol is indicated.

Non-invasive and remote monitoring also is useful to medical personnel to monitor a patient's physiological state while the patient is at home, at a senior center, or otherwise away from a hospital or doctor's office setting. Physiological parameters of the patient could be measured and transmitted to a remote medical office or veterinarian facility, thus minimizing the need for numerous doctor, veterinarian, or hospital visits. Remote monitoring also could indicate whether a patient, whose location is unknown, is dead or alive, such as when a patient is lost under rubble caused by an earthquake, hurricane, or man-made disaster.

However, to be practical in the above-described situations, a device capable of non-invasive and remote monitoring of a patient should be relatively small, comfortable, and wearable for the patient for extended periods. Present-day monitoring devices are often large, cumbersome, stiff, and restrictive and do not allow the patient to move comfortably. Such monitoring devices often extend multiple electronic or biosensor leads from a monitoring station to a patient or require cuffs or bands to be wrapped around the patient. To that end, present-day monitoring devices typically do not have their own power sources, and are required to be connected to an electronic wall socket or generator to operate. This prevents a patient from moving freely, as may be required on a battlefield, when undertaking to operate an aircraft, automobile, or heavy machinery, or even when at home.

Accordingly, it is desirable to provide a small, flexible, non-invasive device for physiological monitoring that permits a patient to move freely and comfortably. In addition, it is desirable to provide a wearable biocybernetic monitoring device that permits wireless remote monitoring of physiological parameters of a patient. It also is desirable to provide a physiological monitoring system that utilizes such devices. Furthermore, other desirable features and characteristics will become apparent from the subsequent detailed description of the embodiments and the appended claims, taken in conjunction with the accompanying drawings and the foregoing technical field and background.

BRIEF SUMMARY

In accordance with an exemplary embodiment, a wireless physiological monitoring device comprises a substrate formed of a flexible biocompatible material, wherein the substrate has a surface for affixing to the skin of a patient. A wireless data transmission device, a biosensor, and a power source are integrated with the substrate. The biosensor is configured to measure a physiological parameter. Flexible conductors are integrated with the substrate and are configured to electrically couple the biosensor with the data transmission device and the power source with the data transmission device.

In accordance with another exemplary embodiment, a wireless device for the remote monitoring of physiological parameters of a patient comprises a biocompatible substrate having a surface configured for the removable affixing to the skin of the patient. A data transmission system for wirelessly transmitting data to a remote data transceiver is physically coupled to the substrate. A power source is configured to supply power to the data transmission system and a light-emitting diode is integrated with the substrate and powered by the power source. Flexible conductors electrically couple the light-emitting diode and the data transmission system and electrically couple the power source and the data transmission system.

In accordance with a further embodiment, a physiological monitoring system comprises a central monitoring station having a transceiver for receiving data transmitted wirelessly and a wireless device for the monitoring of physiological parameters of a patient. The wireless device comprises a substrate formed of a flexible biocompatible material. The substrate has an adhesive surface for affixing to the skin of a patient. A wireless data transmission device is integrated with the substrate and is configured to wirelessly transmit data to the transceiver of the central monitoring station. A biosensor is integrated with the substrate and configured to measure a physiological parameter. A power source is integrated with the substrate and flexible conductors are integrated with the substrate and are configured to electrically couple the biosensor and the power source with the data transmission device.

BRIEF DESCRIPTION OF THE DRAWINGS

Various embodiments will hereinafter be described in conjunction with the following drawing figures, wherein like numerals denote like elements, and wherein.

DETAILED DESCRIPTION

The following detailed description is merely exemplary in nature and is not intended to limit the described embodiments or the application and uses of the described embodiments. Furthermore, there is no intention to be bound by any expressed or implied theory presented in the preceding technical field, background, brief summary or the following detailed description.

Figure 1:
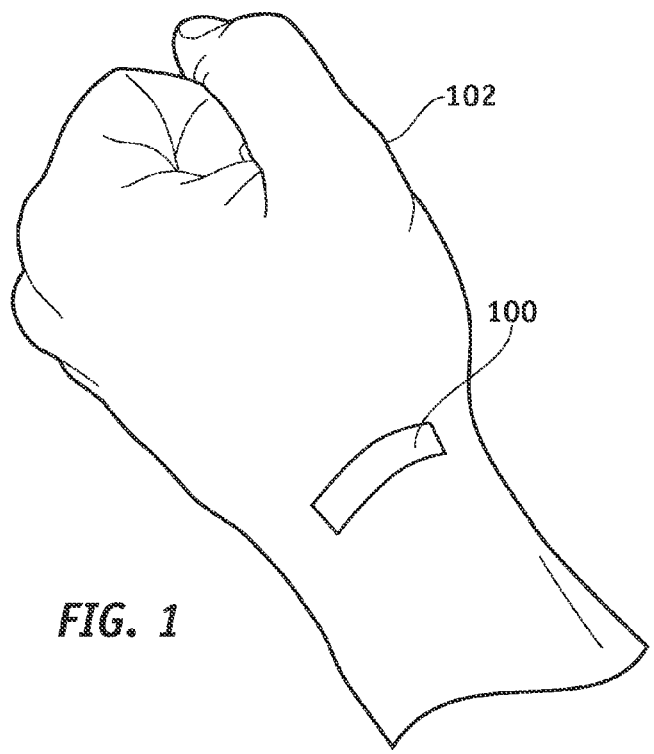
FIG. 1 is an isometric view of a patient wearing a physiological monitoring device, in accordance with an exemplary embodiment.

Referring to FIG. 1, in accordance with an exemplary embodiment, a flexible, non-invasive device 100 for remote physiological monitoring of an animal, such as a human 102, is configured for affixing to the skin of the animal. While it will be understood that device 100 can be used to monitor physiological parameters of any animal that is large enough for affixing of device 100 thereto and from which physiological data may be obtained, such as an animal under veterinarian care or a human being, for convenience the animal will be referred to herein as "the patient". Device 100 may be affixed to any part of the patient from which a desired physiological parameter can be obtained. For example, if pulse of a human is a physiological parameter to be monitored, preferably device 100 is applied to a pulse point of the patient, such as the underside of the wrist or on the neck proximate to the jugular vein.

Figure 2:
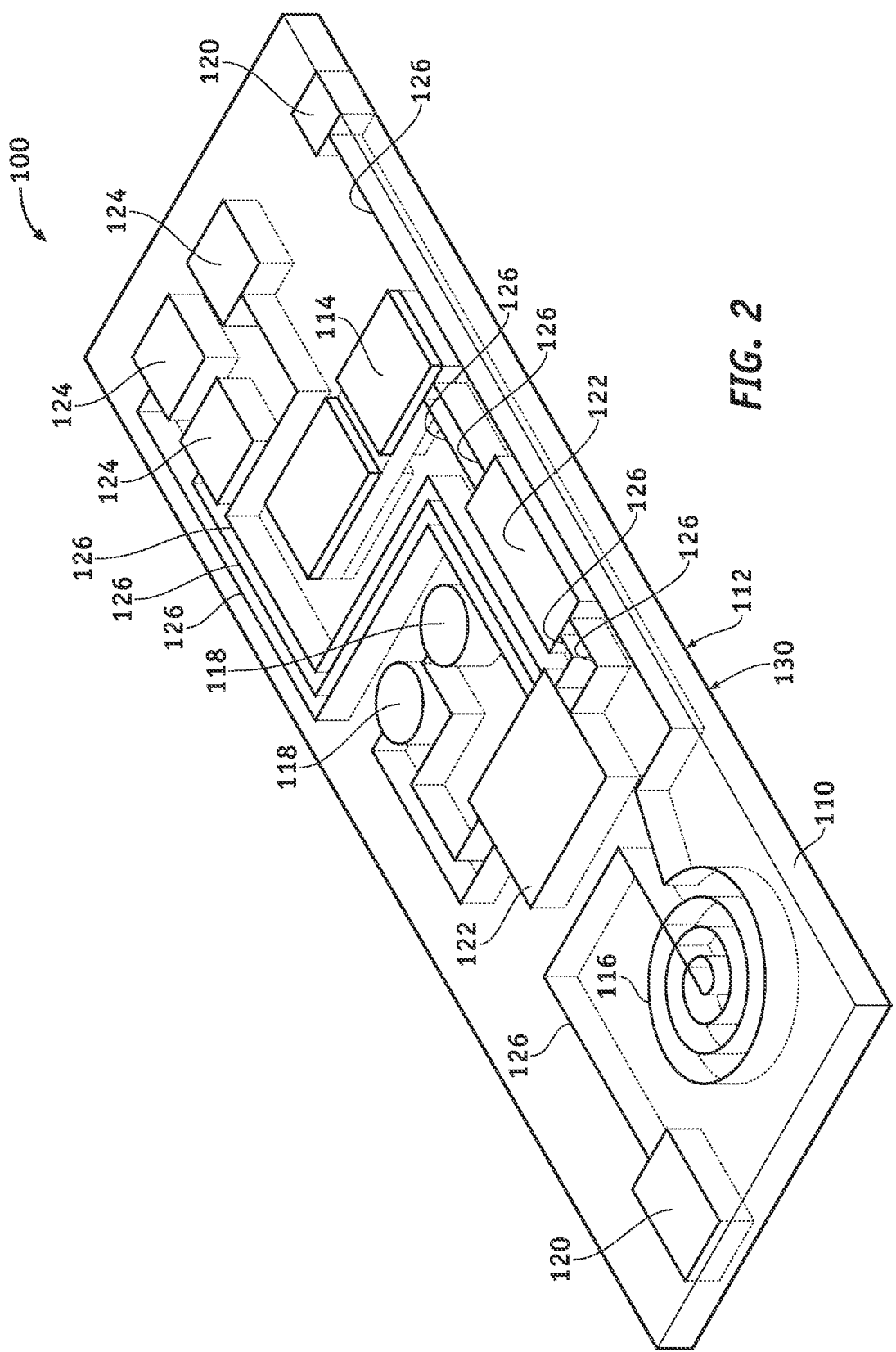
FIG. 2 is an isometric view of a patient monitoring device, in accordance with an exemplary embodiment.

FIG. 2 is a close-up isometric view of device 100 and the components thereof, in accordance with an exemplary embodiment. Device 100 comprises a substrate 110 that is formed of a flexible, biocompatible material having low moisture permeability. Examples of materials from which to fabricate substrate 110 include biocompatible polymers, such as, for example, polyimide or polydimethylsiloxane (PDMS), or other biocompatible materials such as silicon. In a preferred exemplary embodiment, substrate 110 is formed of parylene, particularly parylene C. Parylene is a United States Pharmacopoeia (USP) Class VI biocompatible polymer that can be deposited through a highly conformal vapor deposition process. Parylene is strong and flexible (Young's modulus of approximately 4 GPa), has a low dielectric constant (approximately 3), has a high volume resistivity ($>10^{16}$ ohm-cm), has low moisture permeability, and is easily manipulated using standard microfabrication techniques such as reactive ion etching (RIE). Alternatively, substrate 110 can be formed of any combination of the above materials. Substrate 110 can have any suitable shape, including rectangular, square, circular, oval, and the like. While substrate 110 can have any size suitable for supporting the various components of device 100, discussed in more detail below, preferably substrate 110 is of a size that is comfortable and non-irritating to the patient and that permits free movement of the patient for extended time periods.

Substrate 110 has a surface 112 that is configured so that device 100 can be affixed to the skin of a patient. For example, surface 112 may itself be adhesive or a biocompatible adhesive 130 may be disposed on surface 112. Biocompatible adhesives are well-known and, accordingly, will not be discussed in further detail herein. By affixing device 100 to the patient with an adhesive surface 112, substantial contact between device 100 and the skin of the patient can be made so that physiological parameters are accurately measured. In addition, the patient can comfortably wear the device without being restricted by cumbersome bands or straps. Further, device 100 can be easily removed from the patient when monitoring is complete or when the power source (described in more detail below) is depleted.

In an exemplary embodiment, device 100 comprises a power source 114 that is integrated with substrate 110. As used herein, the term "integrated with" substrate 110 means to be formed or embedded within substrate 110, to be disposed or formed on or overlying substrate 110, or otherwise to be physically coupled to substrate 110. Power source 114 can be any power source that can provide sufficient energy to power the various components of device 100 for a period of time over which the monitoring of physiological parameters is to be conducted. In one exemplary embodiment, power source 114 is one or more small batteries, such as, for example, one or more small lithium batteries. In another exemplary embodiment, power source 114 can include one or more kinetic energy converters, such as, for example, piezoelectric transducers, thermoelectric generators, such as those thermoelectric generators that generate electricity by using temperature difference between the wearer's skin and outside air, and/or electromagnetic generators, such as those electromagnetic generators that generate electricity from rotational torque. If the power source of patient monitoring device 100 is depleted and not recharged, device 100 can be configured as a disposable device that is easily removed from the patient and, optionally, replaced by a new patient monitoring device 100.

In accordance with another exemplary embodiment, device 100 comprises a data transmission system 116 for transmitting physiological parameter data to remote monitoring stations (not shown). Data transmission system 116 is integrated with substrate 110 and can be powered by power source 114. Preferably, data transmission system 116 is a flexible system that does not substantially interfere with or hinder the flexibility of substrate 110. Data transmission system 116 can be, for example, a radio-frequency (RF) system, such as a flexible RF coil system illustrated in FIG. 2, or an infrared (IR) communication system. A flexible RF coil system may be fabricated, for example, by sandwiching an insulating layer of polymer, such as parylene, between two metal layers with a polymer coating on each side of the metal layers. The polymer isolates the coil from the environment while at the same time insuring the material's biocompatibility. Data transmission system 116 also may be configured for power transmission to charge or recharge power source 114.

Device 100, in accordance with an exemplary embodiment, also may comprise any number and type of biosensors 118. For example, device 100 may comprise blood oxygenation/saturation detectors (blood oximeters) 118 that are integrated with substrate 110. The blood oximeters 118 can be powered by power source 114 and are in electrical communication with data transmission system 116. In this regard, when blood oxygen levels are measured by blood oximeters 118, the blood oxygen levels can be electronically transmitted to data transmission device 116 to be wirelessly transmitted to a remote central monitoring station (not shown). Alternatively, biosensors 118 may be sensors configured to measure one or more of body temperature, hydration levels, sweat electrolyte information, electrocardiogram data, heart rate, and the like.

In another exemplary embodiment, device 100 may comprise one or more flexible multi-electrode arrays 120 that are integrated with substrate 110 and powered by power source 114. The multi-electrode arrays 120 can be made with metal conductive lines sandwiched on each side by a flexible polymer, such as parylene. The electrode area can be exposed using standard photolithography and plasma-etching techniques, as are well known in the industry. The multi-electrode array 120 may be integral with a biosensor 118 or may be a stand-alone component. The multi-electrode arrays 120 can sense the biopotentials at the site of application of device 100 and from these biopotentials indicate physiological parameters. For example, a comparison and correlation of these biopotentials could generate heart rate information and/or determine hydration of the body through the analysis of the conductivity of the sweat underlying device 100. Accordingly, when two or more multi-electrode arrays are used, the arrays are separated from each other by a suitable distance so that the arrays can function properly.

Device 100 may further comprise analog/digital application-specific integrated circuits (ASICs) 122 manufactured to perform dedicated functions. For example, the ASICS 122 can be configured as biosensors to measure heart rate, body temperature, or other physiological parameter. The ASICS 122 are integrated with substrate 110, can be powered by power source 114, and are configured to electronically transmit the physiological parameters to data transmission system 116 for transmission to a remote monitoring station.

Device 100 may also comprise other discrete components that are integrated with substrate 110. For example, light-emitting diodes (LEDs) 124 may be integrated with substrate 110 to provide device functionality monitoring, visual health status, communication-link indication, and the like. Similar to the other components described above, LEDs 124 may be powered by power source 114 and may be in electrical communication with data transmission system 116. Other discrete components may include, for example, chip capacitors, central processing units (CPUs), microprocessors and/or controllers, memory modules, analog-to-digital converters, and the like.

The various components of device 110 may be interconnected by flexible conductors 126 integrated with substrate 110. The flexible conductors can be fabricated using any known flexible packaging technique, such as, for example, a chip-level integrated interconnect (CL-I$^2$) technique. By using flexible conductors for interconnection of the components of device 100, device 100 maintains the flexibility of substrate 110, can conform to any suitable part of patient's body, and can be comfortably worn by the patient for extended periods of time. While FIG. 2 illustrates an embodiment of a patient monitoring device 100 comprising various components and an arrangement of those components, it will be understood that various other embodiments of device are not so limited and may comprise any number and type of the above-described components arranged in any suitable configuration.

Figure 3:
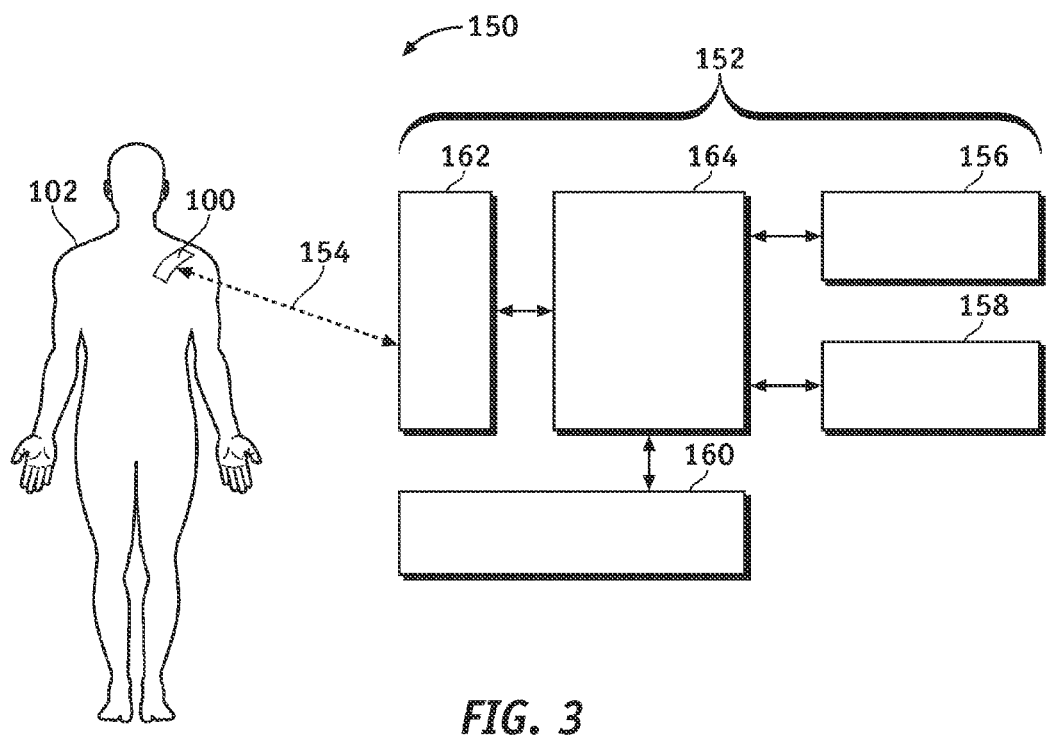
FIG. 3 is a schematic illustration of a physiological monitoring system, in accordance with an exemplary embodiment.

Referring to FIG. 3, a physiological monitoring system 150 for remote monitoring of physiological parameters of a patient includes a patient monitoring device 100 affixed to a patient 102, and a central or base station 152. Patient monitoring device 100 and central station 152 communicate via, for example, a wireless communication link, indicated by dotted line 154, such as a radio frequency (RF) or infrared (IR) communication system. Central station 152 typically includes a wireless transceiver 162, a display system 156, such as, for example, a computer monitor, a printing device 158, and a database system 160. Wireless transceiver 162, display system 156, printing device 158, and database system 160 all connect through block 164. During patient monitoring, physiological data, such as ECG, pulse, body temperature, hydration, blood chemistry, sweat electrolyte levels, and the like are measured by the various biosensors and other components of device 100 described above, and are transmitted wirelessly to central station 152 by wireless communication link 154. Once received by the wireless transceiver 162 of central station 152, the physiological data of patient 102 can be displayed on monitor 156 or printed on hard copy by printer 158 for viewing by medical personnel. The physiological data also can be stored in database system 160 for later retrieval or data manipulation. Central station 152 also can transmit power, instructions, or data to device 100 via wireless communications link 154.

Accordingly, a patient monitoring device and physiological monitoring system that provide for the remote monitoring of physiological parameters of a patient have been provided. The device is flexible and noninvasive, and permits free movement and mobility of the patient while also providing for the transmission of physiological parameters to a remote monitoring location. The physiological parameters can indicate the general health or physical condition of a patient to medical personnel that are not present with the patient. While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

What is claimed is:

1. A wireless physiological monitoring device for monitoring physiological data, comprising:

a substrate formed of a flexible material that is a biocompatible polymer, the substrate further comprising a first surface that is self-adhesive to affix the substrate to skin of a patient;

a wireless data transmission system embedded in the substrate that transmits the physiological data, the wireless data transmission system being a radio-frequency coil system having a coating of a biocompatible polymer material on a first side of the radio frequency coil system and on a second side of the radio frequency coil system and an insulating layer of polymer enclosed between a first and second metal layer, the wireless data transmission system configured to transmit the physiological data to a central monitoring station that is remotely positioned from the wireless physiological monitoring device;

a power source embedded in the substrate that generates power and that powers the wireless data transmission system;

a multi-electrode array embedded within the substrate to sense biopotentials at a site of application of the wireless physiological monitoring device from which to indicate physiological parameters;

a biosensor embedded in the substrate, the biosensor powered by the power source, to measure the physiological parameters;

wherein at least one of the wireless data transmission system, the power source, and the biosensor is microfabricated; and a plurality of conductors embedded within the substrate to form flexible electrical interconnections among the data transmission system, the power source, and the biosensor;

wherein the wireless physiological monitoring device is non-invasive.

2. The wireless physiological monitoring device of claim 1, wherein the biocompatible polymer is selected from one of polyimide, polydimethylsiloxane, parylene, silicon, and a combination thereof.

3. The wireless physiological monitoring device of claim 1, wherein the power source is a thermoelectric generator that generates electricity by using a temperature difference between a site of application of the device and outside air.

4. The wireless physiological monitoring device of claim 1, wherein the power source is a piezoelectric transducer.

5. The wireless physiological monitoring device of claim 1, wherein the power source is an electromagnetic generator.

6. The wireless physiological monitoring device of claim 1, wherein the biosensor further comprises:
a multi-electrode array that functions as a biopotential sensor, wherein the multi-electrode array comprises a plurality of metal conductive lines that are encased by the flexible, biocompatible polymer material of the substrate.

7. The physiological monitoring device of claim 6 wherein the plurality of metal conductive lines are flexible chip-level integrated.

8. The wireless physiological monitoring device of claim 1, wherein the device is applied topically to a surface of the skin.

9. The wireless physiological monitoring device of claim 1, further comprising a light-emitting diode powered by the power source.

10. The wireless physiological monitoring device of claim 1, wherein the biosensor is an application-specific integrated circuit (ASIC) configured to measure a physiological parameter.

11. The physiological monitoring device of claim 1, further comprising:
a light-emitting diode embedded within the substrate and powered by the power source.

12. The wireless physiological monitoring device of claim 1, wherein the power source is a kinetic energy converter.

13. The physiological monitoring device of claim 1 wherein the at least one of the substrate, the wireless data transmission system, the power source, the multi-electrode array, and the biosensor is microfabricated with reactive ion etching.

14. The physiological monitoring device of claim 1 wherein the power source is a self-contained power source.

15. A wireless device for the remote monitoring of physiological parameters, the wireless device comprising:
a substrate formed of at least one biocompatible polymer that is flexible, wherein the substrate comprises a first surface that is self-adhesive to affix the substrate to skin of a patient;
a first multi-electrode array comprising electrode areas that are exposed through an exposure means selected from at least one of a photolithography technique and a plasma etching technique, wherein the multi-electrode array is embedded within the substrate;
a self-contained power source embedded within the substrate that generates power and that powers the multi-electrode array;
wherein the first multi-electrode array is powered by the power source and senses biopotentials at a site of application of the wireless device from which to indicate the physiological parameters;
a wireless data transmission system embedded in the substrate that transmits the physiological data, the wireless data transmission system being a radio-frequency coil system having a coating of a biocompatible polymer material on a first side of the radio frequency coil system and on a second side of the radio frequency coil system and an insulating layer of polymer enclosed between a first and second metal layer, the wireless data transmission system configured to transmit the physiological data to a central monitoring station that is remotely positioned from the wireless physiological monitoring device; and
wherein the wireless device is non-invasive.

16. The wireless device of claim 15, wherein the multi-electrode array comprises a plurality of metal conductive lines that are encased by the flexible, biocompatible polymer.

17. The wireless device of claim 15, wherein the at least one biocompatible polymer is selected from a group consisting of polyimide, polydimethylsiloxane, parylene, silicon and a combination thereof.

18. The wireless device of claim 15, wherein the at least one biocompatible polymer comprises parylene C.

19. The wireless device of claim 15, further comprising a light-emitting diode embedded within the substrate and powered by the power source.

20. The wireless device of claim 19, wherein the first multi-electrode array is a biosensor that is configured to sense biopotentials and measure at least one or more physiological parameters selected from a group consisting of blood oxygen levels, blood chemistry, heart rate, body temperature, hydration levels, sweat electrolyte information, electrocardiogram data, and any combination thereof.

21. The wireless device of claim 15, further comprising a second multi-electrode array that is separated from the first multi-electrode array by a distance to enable proper functioning.

22. A wireless physiological monitoring system for sustained monitoring of human military subjects moving under human power or vehicle transport, in a sustained movement condition, in a non-hospital environment, comprising:
a wireless physiological monitoring device comprising:
a substrate formed of a flexible material that is a biocompatible polymer, the substrate further comprising a first surface that is self-adhesive to affix the substrate to skin of a patient;
a wireless data transmission system embedded in the substrate that transmits physiological parameters, the wireless data transmission system being a radio-frequency coil system having a coating of a biocompatible polymer material on a first side of the radio frequency coil system and on a second side of the radio frequency coil and an insulating layer of polymer enclosed between a first and second metal layer;
a multi-electrode array embedded within the substrate to sense biopotentials at a site of application of the wireless physiological monitoring device from which to indicate physiological parameters;
a self-contained power source embedded in the substrate that powers the wireless data transmission system;

a biosensor embedded in the substrate, the biosensor powered by the power source to measure the physiological parameters;

wherein at least one of the wireless data transmission system, the power source, and the biosensor is microfabricated; and a plurality of flexible conductors embedded within the substrate to form flexible electrical interconnections among the data transmission system, the power source, and the biosensor; and a central monitoring station comprising a transceiver that receives physiological parameters transmitted wirelessly by the wireless physiological monitoring device, wherein the central monitoring station is remotely positioned from the wireless data transmission system;

wherein the wireless physiological monitoring device is non-invasive.

23. The system of claim 22 wherein the wireless physiological monitoring device is configured to be worn by the human wearer as a soldier in a battlefield environment.

24. The system of claim 22 wherein the wireless physiological monitoring device is configured to be worn by the human wearer as a pilot in an aircraft environment.

25. The system of claim 22 wherein the wireless physiological monitoring device is configured to be worn by the human wearer as a machine operator.

26. A wireless physiological monitoring device comprising:

a substrate formed of a flexible biocompatible material, the substrate comprising a surface to affix the substrate to skin of a patient;

a multi-electrode array embedded within the substrate to sense biopotentials at a site of application of the wireless physiological monitoring device from which to indicate physiological parameters, the multi-electrode array comprising electrode areas that are exposed through an exposure means selected from at least one of a photolithography technique and a plasma etching technique;

a wireless data transmission device integrated with the substrate to transmit the physiological parameters, the wireless data transmission device being a radio-frequency coil system having a coating of a biocompatible polymer material on a first side of the radio frequency coil system and on a second side of the radio frequency coil system and an insulating layer of polymer enclosed between a first and second metal layer;

a power source integrated with the substrate to power one or more of the multi-electrode array and the wireless data transmission device; and flexible conductors embedded within the substrate and configured to electrically couple the multi-electrode array and the power source with the data transmission device;

wherein at least one of the wireless data transmission device and the power source is microfabricated.

* * * * *